US011099724B2

(12) United States Patent
Sevenster et al.

(10) Patent No.: US 11,099,724 B2
(45) Date of Patent: Aug. 24, 2021

(54) CONTEXT SENSITIVE MAGNIFYING GLASS

(71) Applicant: KONINKLIJKE PHILIPS N.V., Eindhoven (NL)

(72) Inventors: Merlijn Sevenster, Haarlem (NL); Thomas Andre Forsberg, Hayward, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/337,503

(22) PCT Filed: Sep. 26, 2017

(86) PCT No.: PCT/EP2017/074295
§ 371 (c)(1),
(2) Date: Mar. 28, 2019

(87) PCT Pub. No.: WO2018/065257
PCT Pub. Date: Apr. 12, 2018

(65) Prior Publication Data
US 2019/0286305 A1    Sep. 19, 2019

Related U.S. Application Data

(60) Provisional application No. 62/405,295, filed on Oct. 7, 2016.

(51) Int. Cl.
*G06F 3/0484* (2013.01)
*G16H 30/40* (2018.01)
(Continued)

(52) U.S. Cl.
CPC ....... *G06F 3/04845* (2013.01); *G02B 21/361* (2013.01); *G06F 3/0482* (2013.01); *G06F 3/0484* (2013.01); *G06F 40/169* (2020.01); *G16H 30/20* (2018.01); *G16H 30/40* (2018.01); *G16H 40/63* (2018.01); *G16H 50/20* (2018.01);
(Continued)

(58) Field of Classification Search
CPC .. G06F 3/04845; G06F 40/169; G06F 3/0484; G06F 3/04842; G06F 2203/4805; G06F 2203/4806; G06F 3/0482; G16H 30/40; G16H 50/70; G16H 40/63; G16H 30/20; G16H 50/20; G02B 21/361;
(Continued)

(56) References Cited

U.S. PATENT DOCUMENTS 5,736,974 A    4/1998  Selker
8,438,531 B2 * 5/2013  Majumder ............ G06F 3/0481
716/139
(Continued)

*Primary Examiner* — Vivek D Koppikar

(57) ABSTRACT

A medical imaging system (100) includes a user interface (110) and a magnifying view engine (130). The user interface displays a view of a medical image on a display device (114) and to provide a moveable indicator (116) identifying a moveable point positioned in the displayed medical image. The magnifying view engine (130) generates a localized enlargement of a region of interest within the displayed medical image in response to selection of an existing end
(Continued)

point or an existing contour in the displayed medical image according to a first input by one or more input devices and indicated by a current position of the moveable indicator.

18 Claims, 4 Drawing Sheets

(51) Int. Cl.
    *G16H 50/70*     (2018.01)
    *G16H 40/63*     (2018.01)
    *G16H 30/20*     (2018.01)
    *G16H 50/20*     (2018.01)
    *G06F 40/169*     (2020.01)
    *G02B 21/36*     (2006.01)
    *G06F 3/0482*     (2013.01)
    *G06T 5/00*     (2006.01)

(52) U.S. Cl.
    CPC ......... *G16H 50/70* (2018.01); *G06F 3/04842* (2013.01); *G06F 2203/04805* (2013.01); *G06F 2203/04806* (2013.01); *G06T 5/008* (2013.01); *G06T 2207/20104* (2013.01); *G06T 2207/30004* (2013.01)

(58) Field of Classification Search
    CPC ................... G02B 21/36; G06T 5/008; G06T 2207/20104; G06T 2207/30004; G06T 5/00
    See application file for complete search history.

(56) References Cited

U.S. PATENT DOCUMENTS

| | | | |
|---|---|---|---|
| 8,988,519 B2 | 3/2015 | Mar et al. | |
| 9,665,216 B2* | 5/2017 | Yamamoto | G06F 3/0488 |
| 2005/0068340 A1* | 3/2005 | Lipsky | G11B 27/329 |
| | | | 345/661 |
| 2005/0177783 A1* | 8/2005 | Agrawala | G06F 3/04883 |
| | | | 715/230 |
| 2008/0118237 A1* | 5/2008 | Wegenkittl | G06F 3/0481 |
| | | | 396/76 |
| 2010/0054556 A1 | 3/2010 | Novatzky et al. | |
| 2010/0135562 A1 | 6/2010 | Greenberg et al. | |
| 2011/0058653 A1* | 3/2011 | Baumgart | G06T 19/00 |
| | | | 378/98.2 |
| 2011/0074828 A1 | 3/2011 | Capela et al. | |
| 2012/0206481 A1* | 8/2012 | Endo | G06F 3/0486 |
| | | | 345/619 |
| 2014/0118577 A1* | 5/2014 | Masuda | H04N 5/232 |
| | | | 348/240.2 |
| 2014/0225929 A1* | 8/2014 | Serlie | G06T 3/0006 |
| | | | 345/648 |
| 2014/0365244 A1* | 12/2014 | Lee | G16H 30/20 |
| | | | 705/3 |
| 2016/0140714 A1* | 5/2016 | Hara | G06T 7/0012 |
| | | | 348/189 |
| 2017/0090675 A1* | 3/2017 | Lee | A61B 8/469 |
| 2017/0099431 A1* | 4/2017 | Harada | H04N 5/23216 |
| 2017/0153751 A1* | 6/2017 | Horiike | H04N 1/00795 |

* cited by examiner

CONTEXT SENSITIVE MAGNIFYING GLASS

CROSS-REFERENCE TO PRIOR APPLICATIONS

This application is the U.S. National Phase application under 35 U.S.C. § 371 of International Application No. PCT/EP2017/074295, filed on Sep. 26, 2017, which claims the benefit of U.S. Patent Application No. 62/405,295, filed on Oct. 7, 2016. These applications are hereby incorporated by reference herein.

FIELD OF THE INVENTION

The following generally relates to imaging and more specifically to interpretations and measurements of medical images from modalities, such as computed tomography (CT) reconstruction, positron emission tomography (PET), single photon emission computed tomography (SPECT), magnetic resonance (MR), and combinations thereof.

BACKGROUND OF THE INVENTION

Interpretation of medical images can include quantitative measurements, such as the dimensions of a lesion. For example, in Response Evaluation Criteria In Solid Tumors (RECIST), a measurement is taken across a lesion at a widest point in an image slice or view. That is, the widest part of the lesion is measured. The measurements over time are then used to grade the tumor or provide a status of the tumor, such as progressing or stable. The grade or status of the tumor is typically, according to formal guidelines, then used to determine treatment options for a patient.

Healthcare professionals, such as a radiologist, receive medical images for patients and interpret or read the images. Healthcare professionals are under time pressures to interpret the medical images. Measurements, such as RECIST measurements are typically made by marking a start and end point. However, due to the resolution of a display device displaying the image and a precision of a pointer, such as a mouse cursor relative to the displayed image, placement of end points can introduce error in the measurements. A typical approach to address this is to use a zoom feature. The zoom feature enlarges the image on the display device within physical constraints of the display device, which provide for more precisely placed end points relative to the boundaries of the measured lesion.

The zooming in and out on images interrupts the workflow, and adds time to the process. The zooming in on an image additionally removes from view a portion of the image to accommodate the zoomed image within the constraints of the display device or a window within the display device, which provides context and interpretation relative to the image as a whole. For example, in an image with multiple lesions, zooming in on an image for measurements of a particular lesion, may remove other lesions from view, for which then the healthcare practitioner visually and mentally rescans after zooming back out to reestablish context. The context can include, for example, which lesions are measured and which is next to be measured, adding additional time for the rescanning and reestablishing context.

One approach is to add a tool bar or drop down menu, which adds additional inputs, such as mouse clicks, to select an enlargement and/or measurement tool. Over time this approach adds overhead from the repetitive additional inputs similar to that of the zooming in and out on images.

Another approach to interpretation and measurements is image processing, which automatically identifies and segments lesions in an image using computer based algorithms. The segmented lesions are identified with a contour line from which measurements can be taken. The contoured lesions are presented superimposed on the image, which allow the healthcare professional to adjust the contour lines before a measurement is made, that is, dragging or moving a contour line to better conform to a shape of a lesion. Identifying a better placement of the contour line is often approached with zooming in on the contoured lesion, which presents similar issues to the zooming in for a measurement described above.

SUMMARY OF THE INVENTION

Aspects described herein address the above-referenced problems and others.

The following describes a context sensitive magnifying glass displayed within view of a medical image displayed on a display device. The context sensitive magnifying glass includes a localized enlargement of a region of interest in the displayed medical image. Inputs can be received marking points in the localized enlargement of the region of interest, which are mapped to dimensions of the medical image. Invoking the context sensitive magnifying glass can be in response to currently displayed information and/or inputs from one or more input devices.

In one aspect, a medical imaging system includes a user interface and a magnifying view engine. The user interface displays a view of a medical image on a display device (114) and to provide a moveable indicator (116) identifying a moveable point positioned in the displayed medical image. The magnifying view engine (130) generates a localized enlargement of a region of interest within the displayed medical image in response to selection of an existing end point or an existing contour in the displayed medical image according to a first input by one or more input devices and indicated by a current position of the moveable indicator.

In another aspect, a method of displaying medical images includes displaying a view of a medical image on a display device and providing a moveable indicator identifying a moveable point positioned in the displayed medical image. A localized enlargement of a region of interest within the displayed medical image is generated in response to selection of an existing end point or an existing contour in the displayed medical image according to a first input by one or more input devices and indicated by a current position of the moveable indicator.

In another aspect, a medical imaging system includes a user interface, an intent detection engine, and a magnifying view engine. The user interface displays a view of a medical image on a display device and provides a moveable indicator identifying a moveable point positioned in the displayed medical image. The intent detection engine generates a signal that requests a localized enlargement of the region of interest within the displayed medical image in response to selection of an existing end point or an existing contour in the displayed medical image according to a first input by one or more input devices and indicated by a current position of the moveable indicator and an evaluation of a set of rules that map an evaluation of at least the first input to the generated signal. The magnifying view engine generates the localized enlargement of a region of interest within the displayed medical image in response to the generated signal.

These and other aspects of the invention will be apparent from and elucidated with reference to the embodiment(s) described hereinafter.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
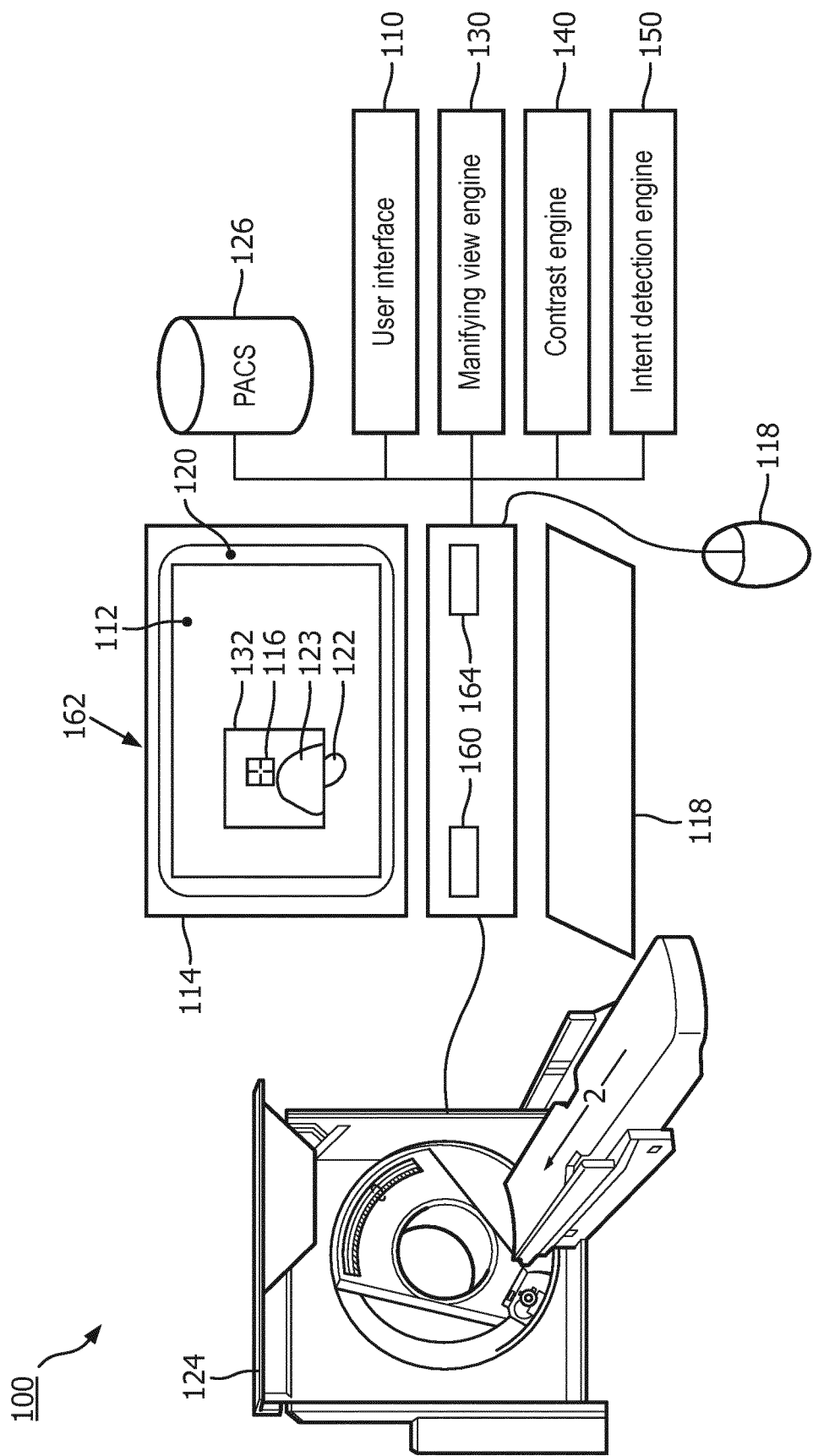
FIG. 1 schematically illustrates an embodiment of a medical imaging system with a context sensitive magnifying view engine.

With reference to FIG. 1, an embodiment of a medical imaging system 100 with a context sensitive magnifying view engine is schematically illustrated. The system 100 includes a user interface 110, which displays a view of a medical image 112 on a display device 114 and provides a moveable indicator 116. The moveable indicator 116 identifies a moveable point positioned in the displayed medical image 112 according to a first input by one or more input devices 118, such as a mouse, keyboard, microphone, touch screen, light pen, combinations and the like. The user interface 110 maps the position of the moveable indicator 116 in a first coordinate system to a second coordinate system of the medical image.

For example, a medical image in a DICOM format can include dimensions which correspond to anatomical positions and sizes of a patient in a first coordinate system, and the display of the medical image changes the dimensions in a second coordinate system, such as with a view or window including the displayed medical image 112 with a zoom factor which enlarges the medical image to fit within a display area 120 of the display device 114. The coordinates, according to the display device 114, the displayed medical image 112, and a position of the moveable indicator 116 are mapped to the coordinate system of the medical image in the DICOM format. Thus, for example, when measuring a lesion 122 in the displayed medical image 112, the measurement is according to the anatomical distances indicated by the DICOM format, and not the physical dimensions of the display device 114 with the magnified portion of the lesion 123.

The displayed medical image 112 can be received directly from a medical imaging scanner 124, such as a computed tomography (CT) scanner, a magnetic resonance (MR) scanner, a positron emission tomography (PET) scanner, single photon emission computed tomography (SPECT) scanner, ultrasound (US) scanner, combinations thereof, and the like. The displayed medical image 112 can be received from a storage subsystem 126, such as a Picture Archiving and Communication System (PACS), radiology information system (RIS), Electronic Medical Record (EMR), Hospital Information System (HIS) and the like. The medical image can include a two or more dimensional medical image, which is displayed in a two dimensional view on the display device 114 as the displayed medical image 112.

A magnifying view engine 130 generates a localized enlargement of a region of interest 132 within the displayed medical image 112 relative to a current position of the moveable indicator 116. The magnifying view engine 130 determines attributes of the localized enlargement of the region of interest, which include a size, a zoom factor, a position and a shape. A localized enlargement includes a magnified area of the displayed medical image 112, which is less than the whole image, such an area less than ten percent of the area of the displayed medical image 112. In some embodiments, the attributes are determined based on user preferences or defaults. In some embodiments, the attributes are determined based on displayed information with the display medical image 112, such as end points of a measurement or a width of area contours of a segmented lesion.

For example, the size of the localized enlargement of the region of interest can be proportional to a distance between existing end points, the zoom factor of the localized enlargement of the region of interest can be inversely proportional to the distance, and/or the position of the localized enlargement of the region of interest can include one of the end points within the displayed medical image. In another example, the distance corresponds to a maximum width across a contoured segmented lesion.

The attributes of the localized enlargement of a region of interest 132 can be modified with inputs from the one or more input devices 118. For example, an input from a mouse wheel can increase or decrease the zoom factor of the localized enlargement of a region of interest 132 currently displayed. The user interface 110 adjusts the mapping to the first coordinate system of the medical image according to the moveable indicator 116 from a third coordinate system within the localized enlargement of a region of interest 132, which is different from the second coordinate system of the displayed medical image 112.

A contrast engine 140 can modify the contrast of the localized enlargement of the region of interest differently from the region of interest in the displayed medical image. In some instances, the contrast can be increased from the non-enlarged displayed region of interest such that the edges of the lesion 122 are more readily apparent. In some instances, the difference in contrast from the surrounding non-enlarged areas of the displayed medical image 112 adds to the focus on the contrasted areas, such as increasing visual attention, while maintaining context relative to the displayed medical image 112 as a whole.

An intent detection engine 150 can generate a first signal that invokes the magnifying view engine 130 to generate the localized enlargement of a region of interest 132 and a second signal that invokes the magnifying view engine 130 to remove the localized enlargement of a region of interest 132. The first and second signals can be implemented using computer call or interrupt functions known in the art. The signals can be evaluated based on rules that map the inputs to the signal.

The first signal can be generated based on currently displayed information, an input and/or attributes from the input, such as a selection of the end point or contour, or a selection of the end point or contour in combination with other inputs. In some instances, the first signal indicates an intended response indicative of a healthcare practitioner attempting to slightly adjust a position of the existing end point or contour. In some instances, the intent is inferred from small and/or proximate movements of the one or more input devices 118 and corresponding movement of the moveable indicator 116. In some instances, unnecessarily invoking the localized enlargement of a region of interest 132 is avoided because for some healthcare practitioners the existing end point is correctly placed, initially, approximately 50% of the time, and unneeded extra inputs and/or actions to remove the localized enlargement of a region of interest 132 for correctly placed end points are avoided, while extra inputs and/or actions to invoke the localized enlargement of a region of interest 132 for an incorrectly placed end point are minimized.

The second signal can be generated based on an input command or positioning the moveable indicator 115 outside of the localized enlargement of a region of interest 132. For example, the magnifying view engine 130 is signaled in response to a mouse position, received as an input that correspond to the moveable indicator 116, which is no longer within the localized enlargement of a region of interest 132. In another example, in response to a keyboard command received by the intent detection engine 150, the magnifying view engine 130 is signaled to remove the localized enlargement of a region of interest 132. Changes in position of the existing end point or contour are displayed corrected in the non-enlarged displayed region of interest 132 after removal of the localized enlargement of a region of interest 132. In other words, the changes to an existing end point indicated in the magnified area are mapped from the magnified area to the anatomical coordinate system, and after removal of the magnified area are mapped from the anatomical coordinate system to the displayed image coordinate system.

The user interface 110, the magnifying view engine 130, the contrast engine 140, and the intent detection engine 150 are suitably embodied by one or more configured processors, such as one or more processors 160 of a computing device 162. The configured processor(s) 160 executes at least one computer readable instruction stored in computer readable storage medium, such as the memory 164 of the computing device 162, which excludes transitory medium and includes physical memory and/or other non-transitory medium to perform the disclosed phase reconstruction, segmentation, mask construction, vessel enhancement, registration, motion estimation, and motion compensated reconstruction techniques. The configured processor may also execute one or more computer readable instructions carried by a carrier wave, a signal or other transitory medium. The computing device 162 can comprise a workstation, laptop, tablet, smart phone, body worn computing device, server, combinations and the like. The lines between components represented in the diagram represent communications paths, which can be wired or wireless.

The computing device 162 includes the display device 114, such as a computer display, projector, body worn display, and the like, and one or more input devices 118, such as a mouse, keyboard, microphone, touch or gesture interface, and the like. The computing device 162 includes the one or more processors 160, such as a digital processor, a microprocessor, an electronic processor, an optical processor, a multi-processor, a distribution of processors including peer-to-peer or cooperatively operating processors, client-server arrangement of processors, and the like.

Figure 2:
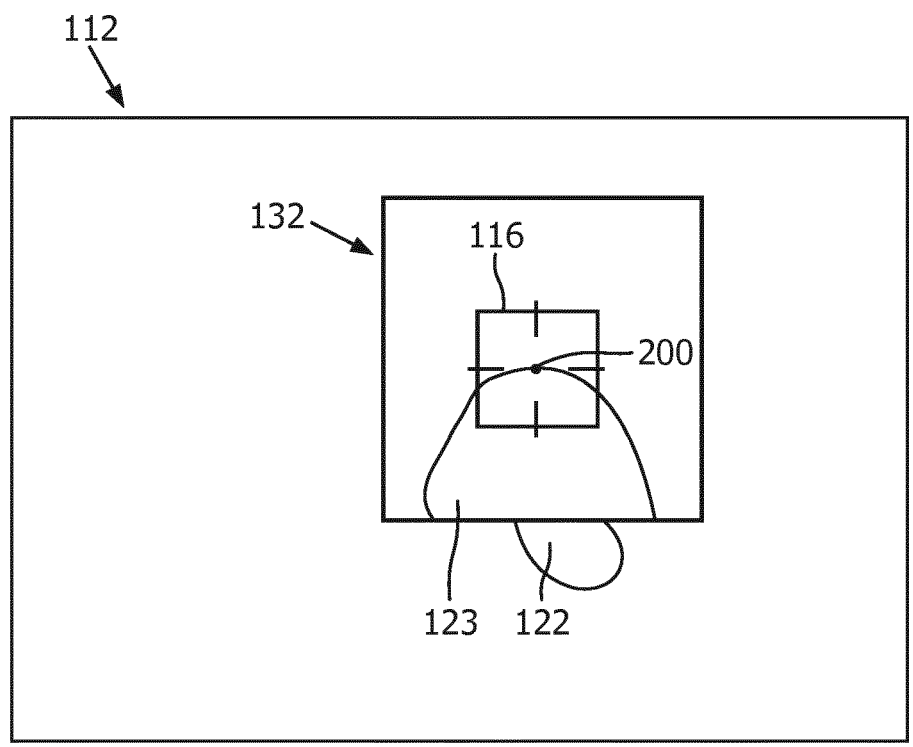
FIG. 2 diagrammatically illustrates an example display of a localized enlargement of a region of interest with an end point at an extremity of a lesion.

With reference to FIG. 2, an example display of the localized enlargement of a region of interest 132 with an end point 200 at an extremity of a lesion 122 is diagrammatically illustrated. The localized enlargement of the region of interest 132 is positioned within the displayed medical image 112. In some instances, the localized enlargement of a region of interest 132 includes only an enlarged portion of the lesion 123, contour, and/or one existing end point of a measurement.

The moveable indicator 116 with an input, such as a mouse click, selects an existing end point 200, such as a previously entered or existing end point, one of two end points used to measure the lesion 122 or an existing contour line. A context is established, which includes the displayed information of an existing end point that is then selected. In some embodiments, the context of selecting an existing end point generates the signal invokes the localized enlargement of a region of interest 132. In some instances, the context reduces the number of inputs and/or actions by the healthcare professional to accurately position an end point, such as automatically zooming in on a particular area of the displayed medical image 112 in a separate window within a window without losing context of a place within the displayed medical image 112.

In some embodiments, the context that generates the first signal to invoke the localized enlargement of a region of interest 132 is in combination of selecting the existing end point and additional inputs, such as in combination with a speed of the moveable indicator, a maximum speed of the moveable indicator, an average speed of the moveable indicator 116, a maximum distance of the current position of the moveable indicator 116 from the selected existing end point, a depressed key or a depressed key for a duration of the one or more input devices 118, and/or a duration of the moveable indicator 116 in a fixed position relative to the selected existing end point. The durations can be compared with a predetermined threshold value that is set greater than a normal response time.

Figure 3:
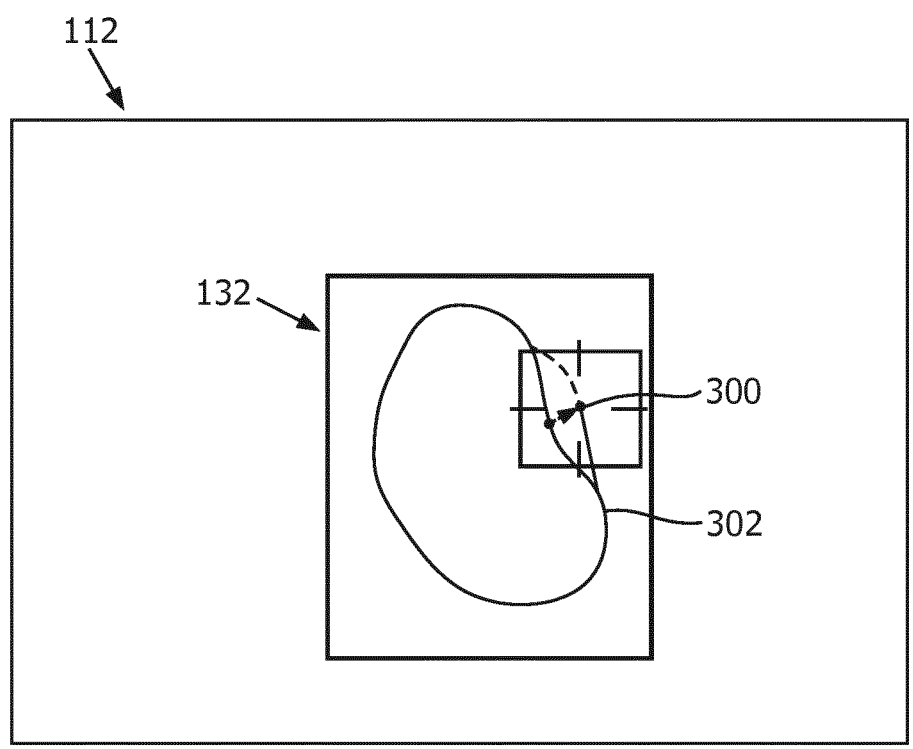
FIG. 3 diagrammatically illustrates an example display of the localized enlargement of a region of interest with a point indicating movement of a segmented lesion contour.

With reference to FIG. 3, an example display of the localized enlargement of a region of interest 132 with a point 300 indicating movement of a segmented lesion contour 302 is diagrammatically illustrated. In some embodiments, the first signal is generated to invoke the localized enlargement of a region of interest 132 based on the displayed information, such as the contour 302 of the segmented lesion. For example, a mouse click within an area defined by the contour 302 invokes the localized enlargement of a region of interest 132. In some embodiments, the attributes of the localized enlargement of a region of interest 132 are determined such that the entire contour 302 is visible within the localized enlargement of a region of interest 132. Changing or repositioning the contour or a portion thereof can be according to algorithms known in the art.

A change in or movement of the contour 302 can be indicated with the moveable indicator 116. For example, selection of a point along the contour with a drag operation can be used to modify the contour. In some embodiments, the input which moves the contour 302 and the input which moves the localized enlargement of a region of interest 132 are based on currently displayed information. For example, a mouse click on a point of the contour 302 and a drag moves the contour 302, while a mouse click within the localized enlargement of a region of interest 132 not within the area defined by the contour 302 and a drag moves the localized enlargement of a region of interest 132. Movements of the one or more input devices 118 repositioning a contour can invoke the localized enlargement of a region of interest 132 similarly to movements re-positioning the existing end point 200 of FIG. 2.

Figure 4:
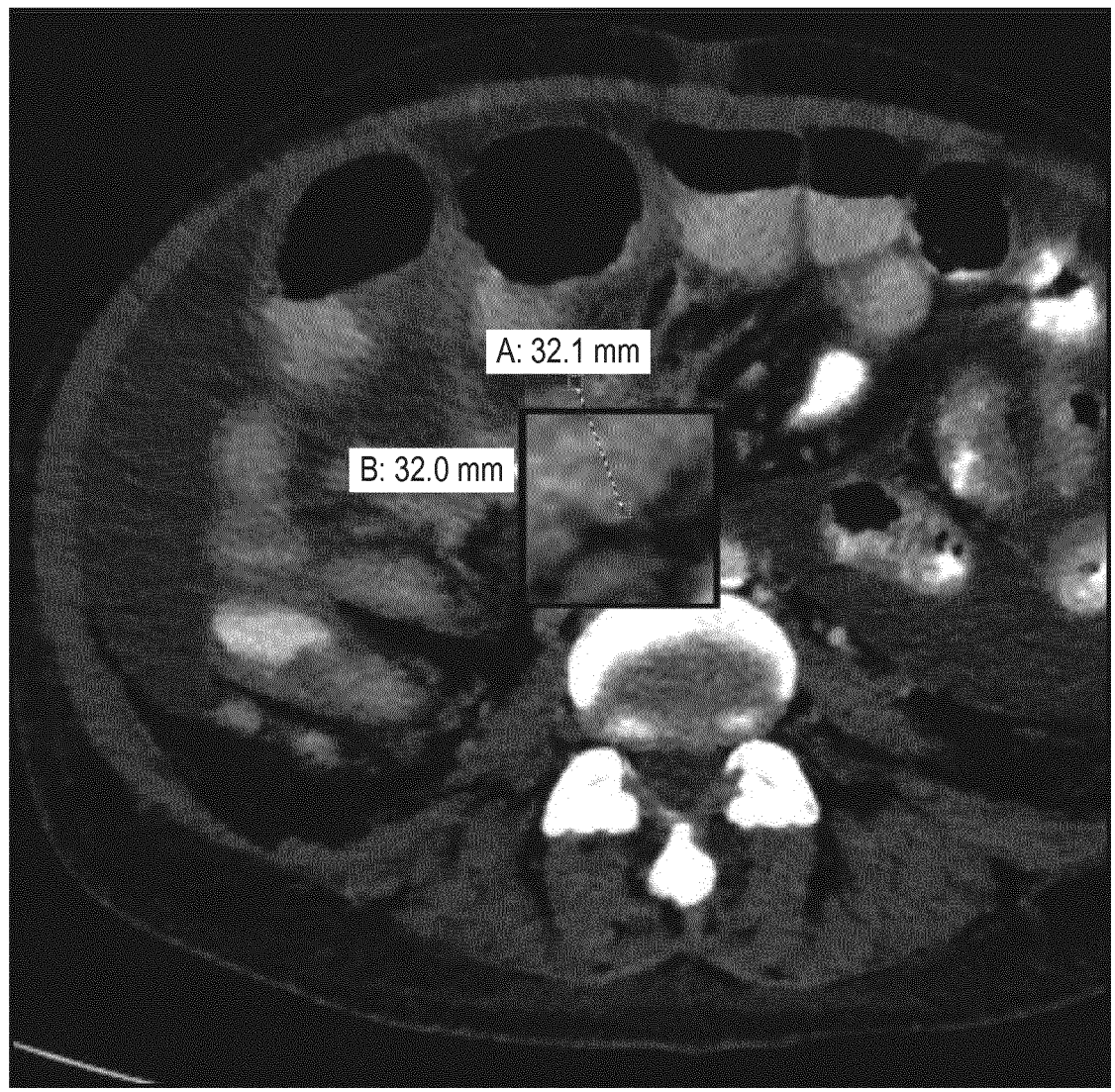
FIG. 4 illustrates an example display of a localized enlargement of a region of interest within a view of an example medical image selecting an existing end point at an extremity of a lesion.

With reference to FIG. 4, an example display of the localized enlargement of a region of interest 132 within a view of an example medical image selecting an existing end point at an extremity of a lesion is illustrated. The displayed medical image includes two measurements: an "A" measurement of 32.1 millimeters (mm), and a "B" measurement of 32.0 mm. The localized enlargement of a region of interest 132 is invoked with a selection of one end point of the two end points of the "A" measurement indicated by a dotted line. The first end point is located outside the localized enlargement of a region of interest 132. The second (selected) end point is located within the localized enlargement of a region of interest 132. The moveable indicator 116 is indicated by an unfilled rectangular shape with a bordered dotted line. The center of the rectangular shape represents a point. In some instances, the unfilled rectangular shape allows the enlarged areas of the displayed medical image 112 to be visually apparent around the point that is not obscured by the moveable indicator 116. The localized enlargement of a region of interest 132 includes a border which separates and distinguishes the enlarged region of interest from remaining areas of the displayed medical image 112.

Rules can be used to invoke the localized enlargement of a region of interest 132, which evaluate attributes of one or more inputs and currently displayed information to generate a signal to invoke the localized enlargement of a region of interest 132. For example, with an input of a mouse click corresponding to a selected end point, X=yes, in FIG. 4. That is, the moveable indicator 116 is positioned to correspond to an existing end point currently displayed when the mouse is clicked. An attribute of the input includes the duration, Y, in milliseconds during which the user modifies the location of the start or end point of the measurement. That is, the end point is being moved to a new position with a drag and the duration of the drag is measured in milliseconds. Another attribute of the input includes an average speed of a mouse tracking, Z mm/s, for a pre-determined window of milliseconds. That is, the attribute of input includes the average speed of the moveable indicator across the displayed medical image 112.

An example rule can include: if X=yes and Y>1000 ms, then invoke localized enlargement of a region of interest 132 or generate the first signal. In some instances, the healthcare professional has paused after selecting an end point, which suggests that magnification would aid. Another example can include if X=yes, Z<threshold and Y>500, then invoke localized enlargement of a region of interest 132 or generate the first signal. In some instances the healthcare professional is moving the moveable indicator 116 slowly for a period of time, in small increments, or in close proximity to the originally positioned end point, which suggests that magnification would aid.

In some embodiments, parameters such as Y and/or Z are configurable. In some embodiments, the system 100 can learn to optimize one or more parameters by analyzing a database of user interactions. Parameter values can be determined and/or modified using statistical or machine learning techniques that minimizes a "false positive" rate, that is, a percentage of cases of invoking localized enlargement of a region of interest 132 without any input indicative of moving a selected end point or fixing a new end point.

Figure 5:
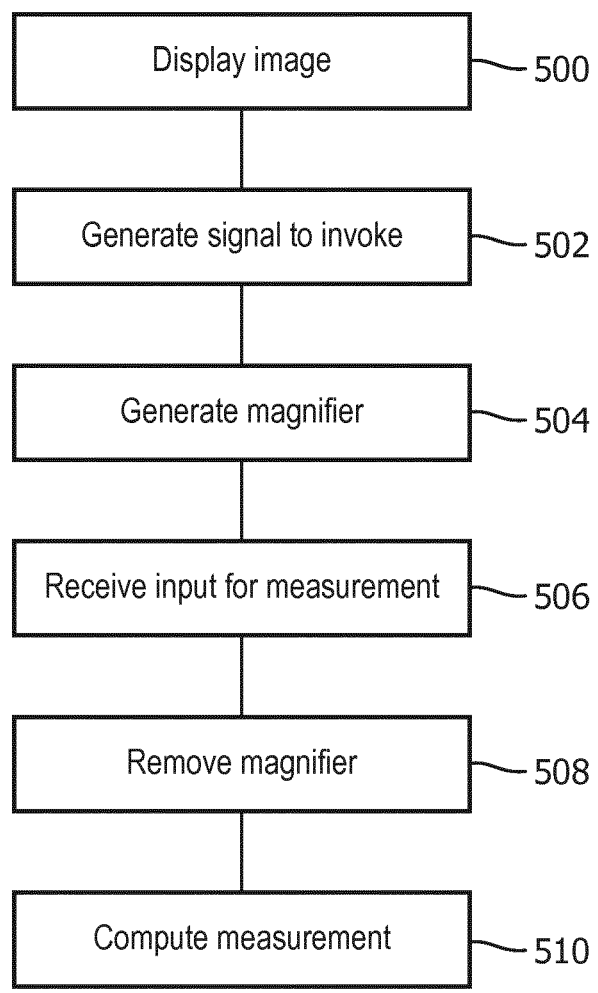
FIG. 5 flowcharts an embodiment of a method of displaying medical images with a context sensitive localized enlargement of a region of interest.

With reference to FIG. 5, an embodiment of a method of displaying medical images with a context sensitive localized enlargement of a region of interest is flowcharted. At 500 a view of a medical image is displayed on the display device 114 and the moveable indicator 116 provides a moveable point positioned in the displayed medical image 112. A first input by one or more input devices 118 selects an existing end point or position of a contour within the displayed medical image, such as a mouse tracking. The displayed medical image 112 can include other displayed information, such as one or more existing end points and/or existing contours.

At 502, a first signal is generated that requests the generated localized enlargement of the region of interest 132 within the displayed medical image 112 according to a second input. The second input can include attributes of a speed of the moveable indicator 116, a time duration, and/or a distance of the moveable indicator 116 from the original or selected existing end point or position selected on the existing contour. The first signal can be in response to selecting an existing end point or contour. The first signal can be in response to selecting an existing end point or contour in combination with another input and/or other input attributes, such as the speed, time duration or distance. The generation of the first signal can use rules that map the second input to the first signal.

At 504, in response to the first signal, the localized enlargement of the region of interest 132 within the displayed medical image 112 relative to a current position of the moveable indicator 116 is generated. Generating the localized enlargement of the region of interest 132 includes determining attributes of a size, a zoom factor, a position and a shape of the localized enlargement of the region of interest 132. The attributes of the localized enlargement of the region of interest 132 can be determined according to a distance between the selected end point and another end point, a width across an area defined by the existing contour, and/or a user or system parameter. The generated localized enlargement of the region of interest 132 can include modifying the contrast of the localized enlargement of the region of interest 132 differently from the region of interest in the displayed medical image 112.

At 506, a third input can be received, which moves an existing end point or contour in the localized enlargement of the region of interest 132. The moved point or contour is mapped from a coordinate system of the localized enlargement of the region of interest 132 to a coordinate system of the medical image. The third input can include indicating the moved point superimposed on the localized enlargement of the region of interest 132, such as a release of a mouse button. The third input can include modifying a contour currently displayed in the localized enlargement of the region of interest 132.

At 508, a second signal is generated to remove the localized enlargement of the region of interest 132 based on a fourth input. The fourth input can be a command, such as a keyboard command. The fourth input can include attributes of the first input, such as a position of the moveable indicator 116 being external to the localized enlargement of the region of interest 132. In some instances, the fourth input can include another inspection of the first input.

At 510, a measurement can be computed, such as a distance between two end points, an area of a contour, a distance based on a contour, and the like. The computed measurement can include displaying the measurement superimposed on the displayed medical image 112. The computed measurement can include a visual indicator, such as a dotted line between end points.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A medical imaging system, comprising:
   a processor configured to implement:
   a user interface to display a view of a medical image on a display device and to provide a moveable indicator identifying a moveable point positioned in the displayed medical image; and
   a magnifying view engine to generate a localized enlargement of a region of interest within the displayed medical image in response to i) a selection of an existing end point of a pair of measurement end points or a point on an existing contour for anatomy of interest in the displayed medical image according to a first input by one or more input devices and a current position of the moveable indicator and ii) a time duration of a movement of the existing end point or existing contour to a different location which meets or exceeds a predetermined threshold,
   wherein the existing end point includes an end point of two previously entered end points of a measurement, and the existing contour includes a previously segmented contour.

2. The system according to claim 1, wherein the magnifying view engine is further configured to generate the localized enlargement of the region of interest in response to a speed of the moveable indicator.

3. The system according to claim 2, wherein the magnifying view engine is further configured to generate the localized enlargement of the region of interest in response to a duration of the moveable indicator in a fixed position relative to the selected existing end point.

4. The system according to claim 3, wherein a position of the generated localized enlargement of the region of interest is relative to a position of at least one selected from a group consisting of a position of the existing end point, a position of the existing end point and another end point, and a position of the existing contour.

5. The system according to claim 3, wherein the processor uses rules that map at least one selected from a group consisting of the first input, the time duration, and the duration of the moveable indicator, to the signal that requests the generated localized enlargement of the region of interest.

6. The system according to claim 1, wherein the magnifying view engine determines a size, a zoom factor, and a shape of the localized enlargement of the region of interest according to a first distance between the selected existing end point and another end point.

7. The system according to claim 6, wherein the magnifying view engine determines a size, a zoom factor, and a shape of the localized enlargement of the region of interest according to a second distance of a width across an area defined by the existing contour.

8. The system according to claim 1, wherein a size of the localized enlargement of the region of interest is proportional to at least one selected from a group of a first distance between the selected existing end point and another end point and a second distance of a width across an area defined by the existing contour.

9. The system according to claim 1, wherein a zoom factor of the localized enlargement of the region of interest is inversely proportional to at least one selected from a group of a first distance between the selected existing end point and another end point and a second distance of a width across an area defined by the existing contour.

10. The system according to claim 1, further including:
    a contrast engine configured to modify the contrast of the localized enlargement of the region of interest differently from the region of interest in the displayed medical image.

11. A method of displaying medical images, comprising:
    displaying a view of a medical image on a display device and providing a moveable indicator identifying a moveable point positioned in the displayed medical image; and
    generating a localized enlargement of a region of interest within the displayed medical image in response to i) a selection of an existing end point of a pair of measurement end points or a point on an existing contour for anatomy of interest in the displayed medical image according to a first input by one or more input devices and a current position of the moveable indicator and ii) a time duration during of a movement of the existing end point or existing contour to a different location which meets or exceeds a predetermined threshold.

12. The method according to claim 11, further including:
    generating a signal that requests the generated localized enlargement of the region of interest within the displayed medical image according to a second input which includes at least one selected from a group consisting of a speed of the moveable indicator, a maximum speed of the moveable indicator, an average speed of the moveable indicator, and a maximum distance of the current position of the moveable indicator from the selected existing end point, wherein generated the localized enlargement of the region of interest is in response to the generated signal.

13. The method according to claim 12, wherein generating the signal includes:
    generating the signal that requests the generated localized enlargement of the region of interest within the displayed medical image according to a third input which includes a duration of the moveable indicator in a fixed position relative to the selected existing end point.

14. The method according to claim 11, wherein a position of the generated localized enlargement of a region of interest is relative to a position of at least one selected from a group consisting of, a position of the existing end point, a position of the existing end point and another end point, and a position of the existing contour.

15. The method according to claim 12, wherein generating the signal includes:
    using rules that map at least one selected from a group consisting of the first input, the second input, and the third input, to the signal that requests the generated localized enlargement of the region of interest.

16. The method according to claim 11, wherein generating a localized enlargement of a region of interest includes:
    determining a size, a zoom factor, and a shape of the localized enlargement of the region of interest according to a first distance between the selected existing end point and another end point.

17. The method according to claim 11, wherein generating the localized enlargement of a region of interest includes:
    modifying the contrast of the localized enlargement of the region of interest differently from the region of interest in the displayed medical image.

18. A medical imaging system, comprising:
    a processor configured to implement:
        a user interface configured to display a view of a medical image on a display device and to provide a moveable indicator identifying a moveable point positioned in the displayed medical image;
        an intent detection engine configured to generate a signal that requests a localized enlargement of the region of interest within the displayed medical image in response to i) a selection of an existing end point of a pair of measurement end points or a point on an existing contour for anatomy of interest in the displayed medical image according to a first input by one or more input devices and a current position of the moveable indicator and ii) a time duration of a movement of the existing end point or existing contour to a different location which meets or exceeds a predetermined threshold; and
        a magnifying view engine configured to generate the localized enlargement of a region of interest within the displayed medical image in response to the generated signal.

* * * * *